(12) United States Patent
Biskeborn et al.

(10) Patent No.: US 9,757,498 B2
(45) Date of Patent: Sep. 12, 2017

(54) BONDED ALUMINA COATING FOR STAINLESS STEEL

(71) Applicant: International Business Machines Corporation, Armonk, NY (US)

(72) Inventors: Robert G. Biskeborn, Hollister, CA (US); Calvin S. Lo, Saratoga, CA (US); Philip M. Rice, Morgan Hill, CA (US); Teya Topuria, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 23 days.

(21) Appl. No.: 15/041,344

(22) Filed: Feb. 11, 2016

(65) Prior Publication Data

US 2016/0158418 A1 Jun. 9, 2016

Related U.S. Application Data

(63) Continuation of application No. 14/283,310, filed on May 21, 2014, now Pat. No. 9,303,307.

(51) Int. Cl.
*B32B 17/10* (2006.01)
*B32B 27/42* (2006.01)
(Continued)

(52) U.S. Cl.
CPC .......... *A61L 31/022* (2013.01); *A61L 27/306* (2013.01); *A61L 31/088* (2013.01);
(Continued)

(58) Field of Classification Search
CPC ... A61L 2400/18; A61L 27/306; A61L 31/088
See application file for complete search history.

(56) References Cited

U.S. PATENT DOCUMENTS

| 4,141,760 A | 2/1979 | Baldi |
|---|---|---|
| 2006/0193889 A1 | 8/2006 | Spradlin et al. |

(Continued)

FOREIGN PATENT DOCUMENTS

| EP | 2204198 A1 | 7/2010 |
|---|---|---|
| WO | 2009061052 A1 | 5/2009 |

OTHER PUBLICATIONS

Azevedo, C., "Characterisation of metallic piercings," Engineering Failure Analysis 10 (2003), pp. 255-263, © 2003 Elsevier Science Ltd.

(Continued)

*Primary Examiner* — Ibrahime A Abraham
(74) *Attorney, Agent, or Firm* — Nicholas D. Bowman

(57) ABSTRACT

A method for manufacturing an alumina-based layer structure having transition regions between layers is disclosed. The method may include ion milling a stainless steel structure surface to partially reduce a metal oxide layer from, and create an exposed portion of, the surface. The method may include oxidizing the exposed portion of the surface to form a crystallized metal oxide bonding layer, growing a crystallized alumina layer onto the metal oxide bonding layer, and diffusing metal from the surface into the crystallized alumina layer, to form a graded aluminate spinel layer. The method may include forming a first transition region from the graded aluminate spinel layer to a crystalline alumina layer, growing the crystalline alumina layer from the first transition region, forming a second transition region from the crystalline alumina layer to an amorphous alumina layer, and growing the amorphous alumina layer from the second transition region.

4 Claims, 3 Drawing Sheets

(51) Int. Cl.

| | | |
|---|---|---|
| A61L 31/02 | (2006.01) | |
| C23C 14/08 | (2006.01) | |
| C23C 14/00 | (2006.01) | |
| A61L 27/30 | (2006.01) | |
| A61L 31/08 | (2006.01) | |
| C23C 28/04 | (2006.01) | |

(52) U.S. Cl.
CPC ...... *C23C 14/0084* (2013.01); *C23C 14/0094* (2013.01); *C23C 14/081* (2013.01); *C23C 28/04* (2013.01); *C23C 28/046* (2013.01); *C23C 28/048* (2013.01); *A61L 2400/18* (2013.01); *A61L 2430/02* (2013.01)

(56) References Cited

U.S. PATENT DOCUMENTS

| | | |
|---|---|---|
| 2007/0207186 A1 | 9/2007 | Scanlon et al. |
| 2010/0143707 A1 | 6/2010 | Sasaoka et al. |
| 2010/0260922 A1 | 10/2010 | Owens et al. |
| 2012/0307396 A1 | 12/2012 | Biskeborn et al. |

OTHER PUBLICATIONS

Balaceanu et al., "Characterization of Zr-based hard coatings for medical implant applications," Surface and Coatings Technology, Mar. 15, 2010, pp. 2046-2050, vol. 204, Issue 12-13, © 2009 Elsevier B.V. D.O.I. 10.1016/j.surfcoat.2009.11.022.

Brohede et al., "A novel graded bioactive high adhesion implant coating," Applied Surface Science 255, 2009, pp. 7723-7728, © 2009 Elsevier B.V. D.O.I. 10.1016/j.apsusc.2009.04.149.

Chevalier et al., "Ceramics for medical applications: A picture for the next 20 years," Journal of the European Ceramic Society, Apr. 2009, pp. 1245-1255, vol. 29, Issue 7, © 2008 Elsevier Ltd. D.O.I. 10.1016/j.jeurceramsoc.2008.08.025.

Falub et al., "In vitro studies of the adhesion of diamond-like carbon thin films on CoCrMo biomedical implant alloy," Acta Materialia, pp. 4678-4689, vol. 59, Issue 11, © 2011 Acta Materialia Inc. D.O.I. 10.1016/j.actamat.2011.04.014.

Holzapfel et al., "How smart do biomaterials need to be? A translational science and clinical point of view," Advanced Drug Delivery Reviews, pp. 581-603, vol. 65, Issue 4, © 2012 Published by Elsevier B.V. D.O.I. 10.1016/j.addr.2012.009.

Mandrino et al., "Study of oxide protective layers on stainless steel by AES, EDS, and XPS," Surface and Interface Analysis, pp. 285-289, © 2008 John Wiley & Sons, Ltd. D.O.I. 10.1002/sia.2718.

Palraj et al., "Soft Tissue Anaplastic Large T-Cell Lymphoma Associated with a Metallic Orthopedic Implant: Case Report and Review of the Current Literature," Journal of Foot and Ankle Surgery, Nov. 2010, pp. 561-564, vol. 49, Issue 6, © 2010 by the American College of Foot and Ankle Surgeons. D.O.I. 10.1053/j.jfas.2010.08.009.

Shih et al., "Effect of surface oxide properties on corrosion resistance of 316L stainless steel for biomedical applications," Corrosion Science 46 (2004), pp. 427-441, © 2003 Elsevier Ltd. D.O.I. 10.1016/S0010-938X(03)00148-3.

Tiwari et al., "Development and characterization of sol-gel silica-alumina composite coatings on AISI 316L for implant applications," Surface and Coatings Technology, May 21, 2007, pp. 7582-7588, vol. 201, Issue 16-17, © 2007 Elsevier B.V. D.O.I. 10.1016/j.surfcoat.2007.02.026.

Wang et al., "Thermite reactions: their utilization in the synthesis and processing of materials," Journal of Materials Science 28, 1993, pp. 3693-3708, © 1993 Chapman & Hall.

Zarone et al., "From porcelain-fused-to-metal to zirconia: Clinical and experimental considerations," Dental Materials, Jan. 2011, pp. 83-96, vol. 27, Issue 1, © 2010 Academy of Dental Materials. D.O.I. 10.1016/j.dental.2010.10.024.

Bandyopadhyay et al., "Compositionally Graded Aluminum Oxide Coatings on Stainless Steel Using Laser Processing", Journal of the American Ceramic Society, vol. 90, No. 7, pp. 1989-1991, Jul. 2007.

Donik et al., "Initial oxidation of duplex stainless steel", Applied Surface Science, vol. 255, Issue 15, May 15, 2009, pp. 7056-7061.

Biskeborn et al., "Bonded Alumina Coating for Stainless Steel", U.S. Appl. No. 14/283,310, filed May 21, 2014.

List of IBM Patents or Patent Applications Treated as Related, Feb. 9, 2016, 2 pages.

BONDED ALUMINA COATING FOR STAINLESS STEEL

BACKGROUND

The present disclosure generally relates to coatings of stainless steel objects. In particular, this disclosure relates to designed alumina-based coatings formed on surfaces of medical-grade stainless steel objects.

Stainless steel (also known as inox or "inoxydable" steel) is a steel alloy which may have a minimum of 10.5% chromium content by mass. Stainless steel may not readily corrode, rust or stain with exposure to water or other fluids, and may incorporate metallic elements (other than iron (Fe)) including, but not limited to, chromium (Cr), nickel (Ni), and molybdenum (Mo), which may be useful in increasing the steel's resistance to corrosion. Various grades and surface finishes of stainless steel may be used in particular environments that an alloy may endure. Stainless steel may be used in applications where both the mechanical/structural properties of steel and resistance to corrosion are useful.

"Medical grade" or "surgical" stainless steel may be informal terms which may refer to certain grades of stainless steel that may be used in biomedical applications. Common types of stainless steels referred to as "medical grade" may include austenitic 316, 316L and 316LVM. 316, 316L and 316LVM steels may be chromium, nickel and molybdenum alloys of steel that exhibit relatively high strength and corrosion resistance and may be a common material choice for biomedical implants and equipment that are put under pressure. For example, bone fixation screws, prostheses and body piercing jewelry may be formed from austenitic 316L and 316LVM steel. 316 steel may also be used in the manufacture and handling of food and pharmaceutical products, where it may be often required to minimize metallic contamination.

Aluminum oxide, commonly known as "alumina", is a chemical compound of aluminum and oxygen with the chemical formula $AL_2O_3$. It is the most commonly occurring of several aluminum oxides, and specifically identified as aluminum (III) oxide. Alumina may be a ceramic, crystalline material having a high hardness and a high melting point. Alumina may possess properties which may be useful in biomedical applications and dental implants, such as being bio-inert (having low chemical reactivity with bodily tissues and fluids) and mechanical properties such as relatively high stability, hardness, and resistance to wear.

SUMMARY

Various aspects of the present disclosure may be useful for forming designed, high adhesion strength alumina-based surfaces on stainless steel objects used for medical applications. A stainless steel object, such as a surgical implant or medical instrument manufactured according to embodiments of the present disclosure may have a high-hardness coating that has limited chemical and biological reactivity with bodily fluids and/or tissues. A surgical implant or medical instrument manufactured according to embodiments may be useful in limiting biological reactions to stainless steel oxides while exhibiting high-strength characteristics of stainless steel.

Embodiments may be directed towards a method for manufacturing, in a deposition chamber, an alumina-based layer structure having transition regions between layers. The method may include milling, in-situ, a stainless steel structure with an ion beam controlled by a set of parameters that cause the ion beam to remove carbon-based contaminants and at least partially reduce a metal oxide layer from a surface of the stainless steel structure, to create an exposed portion of the stainless steel structure. The method may also include crystallizing, by oxidizing, the exposed portion of the stainless steel structure to form a crystallized metal oxide bonding layer. The method may also include forming, by growing a crystallized alumina layer onto the metal oxide bonding layer and diffusing metal from the stainless steel surface into the crystallized alumina layer, a graded aluminate spinel layer on the crystallized metal oxide bonding layer. The method may also include forming a first transition region from the graded aluminate spinel layer to a crystalline alumina layer, growing the crystalline alumina layer from the first transition region, forming a second transition region from the crystalline alumina layer to an amorphous alumina layer, and growing the amorphous alumina layer from the second transition region.

Embodiments may also be directed towards an apparatus. The apparatus may include a stainless steel structure and an at least partially polycrystalline alumina-based layer structure bonded to an exposed portion of the stainless steel structure. The layer structure may include a crystallized metal oxide bonding layer formed on the exposed portion of the stainless steel structure, and a graded aluminate spinel layer formed on the crystallized metal oxide bonding layer. The graded aluminate spinel layer may have metal diffused from the stainless steel surface, and an at least partially polycrystalline structure. The layer structure may also have a first transition region extending from the graded aluminate spinel layer to a crystalline alumina layer, the crystalline alumina layer formed from the first transition region, a second transition region extending from the crystalline alumina layer to an amorphous alumina layer, and the amorphous alumina layer formed from the second transition region.

Aspects of the various embodiments may be used providing high-strength (atomic) bonding between a stainless steel surface and an amorphous alumina coating due to a continuously graded structure between the stainless steel and the amorphous alumina coating. Aspects of the various embodiments may also be useful for providing a hard, wear-resistant, bio-entered outer coating for use on medical implants, such as prosthetic joints, by using existing and proven material processing practices, machining and fabrication technologies.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
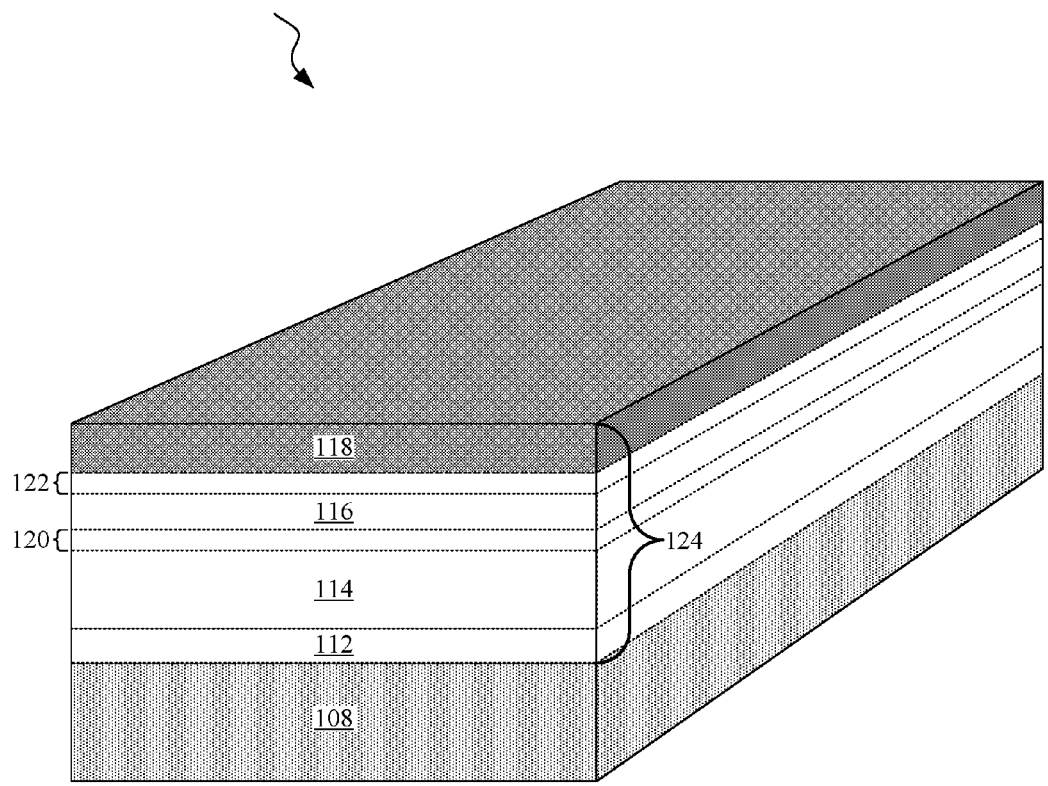
FIG. 1 is an isometric drawing of an alumina-based layer structure bonded to a surface of a stainless steel substrate, according to embodiments of the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

In the drawings and the Detailed Description, like numbers generally refer to like components, parts, steps, and processes

DETAILED DESCRIPTION

Certain embodiments of the present disclosure can be appreciated in the context of providing a high adhesion-strength, high hardness, bio-inert coating for medical devices such as surgical implants, and for stainless steel items such as rings and body-piercing jewelry, which may be in contact with bodily fluids and/or tissues. Surgical implants according to embodiments may be used to provide, for example, increased bodily structural support and joint articulation, while controlling or eliminating adverse biological (chemical) reactions to the implant. Surgical implants according to embodiments may include but are not limited to replacement (prosthetic) joints such as hip, knee and shoulder joints, and reinforcing structures such as bars, pins, nails, screws and buttress plates. While not necessarily limited thereto, embodiments discussed in this context can facilitate an understanding of various aspects of the disclosure.

Certain embodiments may also be directed towards other equipment and associated applications, such as medical instruments. Medical instruments manufactured according to embodiments may provide little (or no) adverse biological (chemical) reactions to the contact of such instruments with bodily fluids or tissues during medical procedures. Medical instruments according to embodiments may include but are not limited to forceps, scalpels, scissors, tweezers, needle holders and laboratory probes.

Embodiments may also be directed towards non-medical applications such as equipment used in conjunction with nuclear reactors, marine environments, and food or chemical processing applications, to provide a high adhesion strength, chemically inert coating. Such coating may be resistive to chemically corrosive environments, and may be used to control (limit) contamination that may occur through the dispersion of metallic oxides from stainless steel equipment, and to protect a stainless steel surface from corrosion and pitting.

For ease of discussion, the term surgical implant is used herein, however, it is understood that various embodiments may also be useful with regards to other medical applications such as medical instruments and jewelry items such as rings and body piercing hardware.

Various embodiments of the present disclosure relate to an alumina-based coating formed on the surface of a stainless steel object, which may provide a high-strength, reliable, bio-inert layer having high hardness, on an outer surface of the object. The stainless steel object may be therefore be useful for providing mechanical stability and support in biomedical applications such as replacement joints, and various types of surgical inserts used for mechanical and structural support. Structurally stable and long-term reliable, biologically non-reactive performance of a surgical implant may result from the use of a stainless steel object having an alumina-based coating.

A graded alumina-based coating, having high bond strength to a stainless steel object, such as a surgical implant, may be useful in preventing delamination, peeling and cracking of the alumina-based coating while it is exposed to bodily tissues and fluids. Structural integrity of the alumina-based coating may help reduce adverse bodily reactions to metallic oxides (of the stainless steel object) and particles shed from the alumina-based coating.

A surgical implant designed according to certain embodiments may be compatible with existing and proven surgical implants, and may be a useful and cost-effective way to protect a patient outfitted with the implant from harmful bodily reactions, and may prevent or eliminate the replacement of a defective surgical implant.

Medical/surgical grade stainless steel (austenitic 316, 316L and 316LVM, for example) has been used for biomedical applications because of its workability, high tensile strength, ductility, hardness, economic advantages, general resistance to wear and corrosion and its general biocompatibility. Stainless steel may be readily formed and machined into a desired shape for a particular medical application. Biomedical applications of stainless steel may include, but are not limited to, load-bearing or structural (reconstructive) implants, artificial joints, and medical instruments. Medical/surgical grade stainless steel may also be used for aesthetic applications such as rings and body-piercing jewelry.

A variety of physiological reaction types have been reported as a result of (often prolonged) contact between stainless steel objects and bodily fluids/tissues. Reaction types may include toxic, hypersensitive, allergenic, autoimmune and carcinogenic reactions, which may result in tissue inflammation, organ poisoning or injury, and/or bodily rejection of an implant device. Metallic ions and oxides, for example nickel or nickel oxide, originating from corrosion (oxidizing) of the stainless steel, due to exposure to liquids and electrolytes, may cause at least some of the reported adverse effects.

When stainless steel implants are used for extended periods of time or have bearing or sliding surfaces, e.g., artificial joint implants, where an abrasive wear processes may be particularly intense, particles or debris (metallic oxides and ions) may be shed from the implants. As this debris is disposed to surrounding tissue, it may be encapsulated, promoting inflammatory reactions and degradation of the tissue, which may eventually lead to pain and early loosening of the implant. Metallic oxides and ions may also start to dissolve and diffuse into the bloodstream, which may lead to additional reaction symptoms.

Ceramic materials may be used as a structural material for surgical implants, due to their hardness and strength properties, and may be more wear resistant than metallic implants. Ceramic implants may be able to withstand heavy work loads, and may not corrode in response to contact with bodily fluids and tissues. Ceramic materials may be stiffer and more brittle than metallic materials, and may therefore, when used as structural bulk material in implants, be more prone to detrimental breaks and fractures than a similar implant formed from metallic materials.

A structurally robust, surgical implant may be constructed by using a stainless steel alloy as a base or substrate material for the implant, and modifying its surface. One approach may include modifying the substrate surface through processes such as ion implantation, gas nitriding and high temperature oxidation. However, this approach may have limitations, such as yielding insufficient surface hardness for long-term wear applications, being prohibitively expensive, and not being feasible for use with a variety of desirable substrate materials.

Another approach for designing a material for medical implants may be to apply a ceramic coating to the surface of a metal or metal alloy surface, either to the whole implant or restricted to the surface areas that are most exposed to abrasive wear. An alumina ($AL_2O_3$) coating may provide a fatigue-resistant surface to a metal substrate which is resilient but sensitive to abrasion. An alumina-based coating may be used to protect a patient's body from direct contact with metallic medical implants, instruments and jewelry items. The bio-inert alumina coating may provide a biologically non-reactive barrier between bodily fluids and/or tissues and stainless steel, and may prevent oxides from the stainless steel from being formed and entering bodily tissues and fluids.

A layer structure having an outer layer of aluminum oxide ($AL_2O_3$) and an intermediate layer comprising titanium nitride (TiN), titanium carbonitride (TiCN) or titanium oxycarbonitride (TiCNO) may be formed on the surface of the various alloys, however this type of layer structure may start to wear down and peel after prolonged use in artificial joints or other types of medical implants. Peeling or delaminating may result in shed debris and exposing only tissues to the substances of the substrate, and may also lead to a dramatic increase the rate of the wear process, should be degree become trapped between sliding/mating surfaces. The tendency to peel or delaminate may depend on the mechanical properties of both the substrate and the coating, and on how the coating is bonded to the underlying substrate.

Certain embodiments relate to the formation of an alumina-based coating having a high bond strength to a medical-grade stainless steel surface, as a result of a continuously graded crystalline interface between the stainless steel surface and the alumina coating.

FIG. 1 is an isometric drawing of an alumina-based layer structure 124, having an amorphous alumina layer 118, bonded to a surface of a stainless steel substrate 108, according to embodiments of the present disclosure. Alumina-based layer structure 124 may be generally useful as a high-strength, bio-inert coating for surgical implants, medical instruments, jewelry and body piercing hardware, according to embodiments of the present disclosure.

The process used in forming the alumina-based layer structure 124 may yield a continuously graded, at least partially polycrystalline structure, having transition regions between layers, which may result in layer structure 124 having high hardness, durability and resistance to abrasive wear, cracking, peeling, and delamination from the stainless steel substrate 108. The bio-inert properties of the amorphous alumina layer 118 may make it suitable to shield bodily tissues and fluids from metallic ions, oxides, and particles shed from the stainless steel substrate 108, according to embodiments. The shielding effect of the alumina-based layer structure 124 may be useful in minimizing or reducing adverse bodily reactions to devices such as surgical implants or medical instruments, and may help to reduce the number of implants that may need to be replaced, as a result of adverse reactions.

The stainless steel substrate 108 may include "medical" or "surgical" stainless steels including, but not limited to grades such as AISI 316, 316L, 316LVM, which may be chosen for biomedical applications, according to embodiments. The crystallized metal oxide bonding layer 112, formed on stainless steel substrate 108, may contain crystalline structures that may be useful as seeds for subsequent alumina crystallization. The graded aluminate spinel layer 114 may share crystalline structures with metal oxide bonding layer 112, and may be useful as an intermediate layer between metal oxide bonding layer 112 and a subsequent alumina layer. The first transition region 120 may be a graded transition between the graded aluminate spinel layer 114 and adjacent layers, and may contribute to the overall structural integrity of the alumina-based layer structure 124. The crystalline alumina layer 116 may share crystalline structures with the first transition region 120, and may be useful as an intermediate layer between the graded aluminate spinel layer 114 and a subsequent amorphous alumina layer.

The second transition region 122 may be a graded transition between the graded crystalline alumina layer 116 and a subsequent amorphous alumina layer, and may contribute to the overall structural integrity of the alumina-based layer structure 124. The amorphous alumina layer 118 may have bio-inert properties which may make it suitable to shield bodily tissues and fluids from metallic ions, oxides, and particles from the stainless steel substrate 108, according to embodiments.

Figure 2:
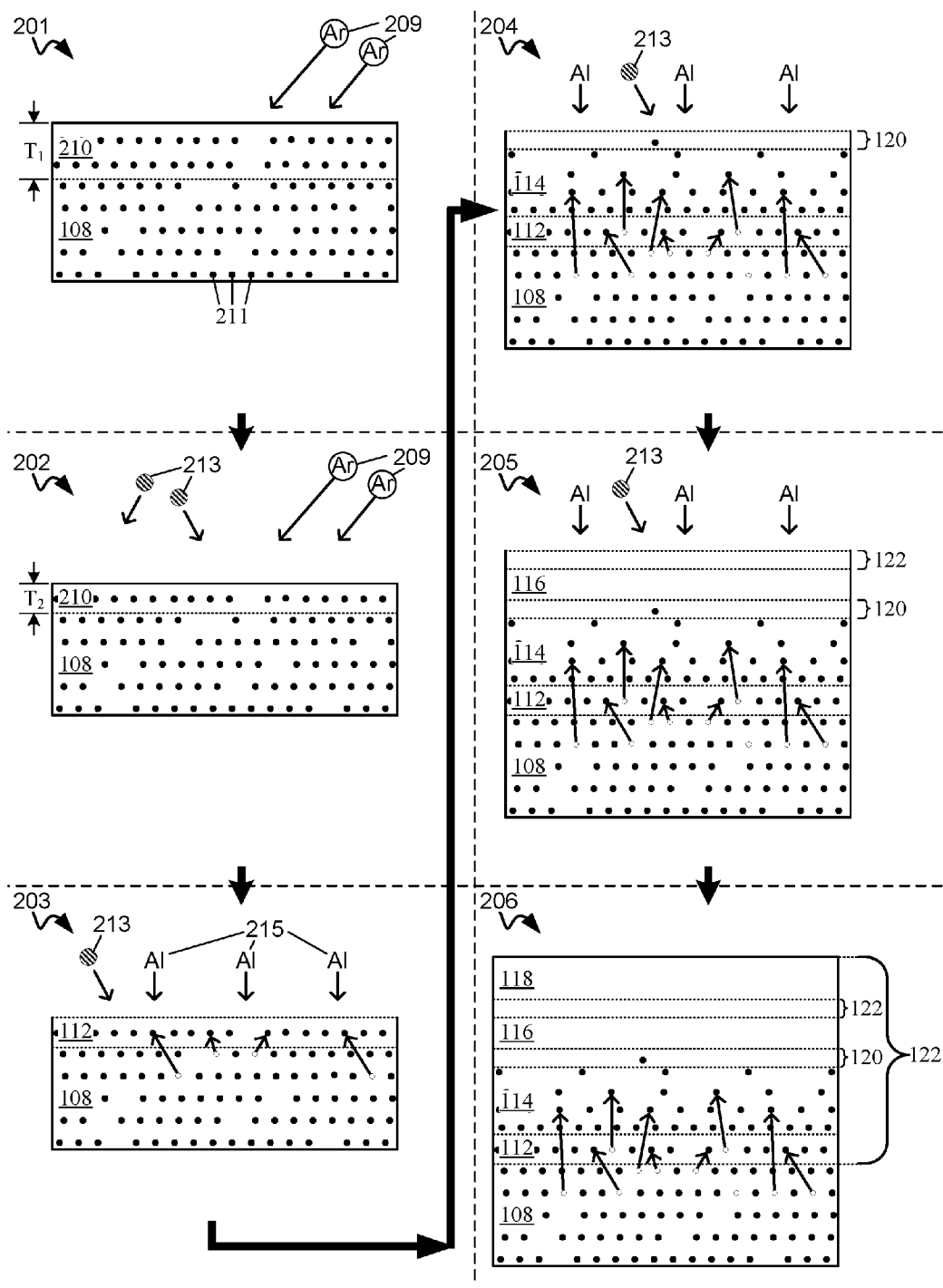
FIG. 2 includes six cross-sectional views depicting the results of processes for bonding an alumina-based layer structure to a surface of a stainless steel substrate, according to embodiments.

FIG. 2 includes six cross-sectional views (201 through 206), consistent with FIG. 1, depicting the expected results of a set of processes for bonding an alumina-based layer structure 124 (FIG. 1) to a surface of a stainless steel substrate 108 (FIG. 1), according to embodiments. These views illustrate an example process; other views and processes may be possible. An alumina-based layer structure formed by these processes may be consistent with layer structure 124 (FIG. 1) and may have a high-strength (atomic) bond to a stainless steel surface, consistent with a bond between layer structure 124 (FIG. 1) and stainless steel substrate 108.

The progression depicted in cross-sectional views 201 through 206 begins with a stainless steel substrate 108, in an initial state, having a metal oxide layer 210 (view 201), which may also include carbon-based contaminants such as naturally occurring organic matter. Cross-sectional views 202 through 206 each depict the results of one or more operations on the stainless steel substrate 108 and/or alumina-based layer structure (124, FIG. 1). The progression ends with a completed alumina-based layer structure 124 (view 206) bonded to the stainless steel substrate 108 (view 206).

Process operations associated with views 201 through 206 may include, but are not limited to ion milling, crystalline layer growth, layer oxidation, reactive sputter deposition of alumina, and metallic diffusion. The results of one or more process operations may be depicted in each view. For example, a view may depict the formation of one or more alumina-based layers, which may include process operations of reactive sputter deposition, metallic diffusion, and crystalline layer growth. The process operations described herein may be carried out in a deposition chamber, under a partial vacuum condition.

Views 201 through 206 depict the formation of individual layers, such as a crystallized metal oxide bonding layer and a graded aluminate spinel layer, as well as the transition (gradient) regions between individual layers. The transition (gradient) regions between individual layers may indicate a structural merging of individual layers, which may result in high-strength bonding of the individual layers to adjacent layers, and of the alumina-based layer structure 124 (FIG. 1) to the stainless steel substrate 108.

Completed structures may be generally shown in the views as having rectangular cross-sectional profiles, with surfaces parallel to each other. This depiction, however, is not limiting; layers may be of any suitable shape, size and profile, in accordance with specific design criteria, manufacturing process limitations and tolerances for a given application. The results of the process operations illustrated may not necessarily be drawn to scale, or be proportional to actual processed layer structure dimensions. For example, interfaces between layers depicted as level and regular, may be sloped or irregular, and relative dimensional ratios may vary from those depicted in the figures. Layer thicknesses shown may be drawn for ease of illustration, and may not necessarily have dimensions proportional to actual processed dimensions.

View 201 depicts a stainless steel substrate 108 having a layer 210 which may include amorphous native metal oxides and carbon-based contaminants. Carbon-based contaminants may include various forms of naturally occurring organic carbon compounds. The amorphous native metal oxides may include oxides of various metals comprising the stainless steel substrate 108, including but not limited to nickel oxide, magnesium oxide and chromium oxide. Thickness T1 depicts an initial thickness of layer 210 before any ion milling operation.

Ion milling of a stainless steel structure, which may include stainless steel substrate 108 and layer 210, may remove the carbon-based contaminants, and reduce amorphous native metal oxides found on the surface of the stainless steel substrate 108, and may be useful to clean and expose a portion of the stainless steel structure (stainless steel substrate 108 and layer 210) that can support structurally stable crystalline oxide and alumina growth.

Ion milling of a surface of the stainless steel structure may be performed using an inert gas, for example, argon 209, which may be injected into the deposition chamber, and accelerated towards the stainless steel structure surface. A set of ion milling parameters may be used to specify a particular ion beam incidence angle normal to the stainless steel structure surface, to specify an ion beam energy, in electron-volts (eV), and to specify an ion milling time interval. For example, an ion beam incidence angle may be between 45° and 70° to a local normal of the stainless steel structure surface, an ion beam energy may be between 250 (eV) and 500 eV, and the ion beam milling duration may be approximately 10 minutes. TRIM (TRansport of Ions in Matter) simulations may be used to simulate and determine a set of ion milling parameters suitable for removal of particular types and thicknesses of amorphous native metal oxides and carbon-based contaminants.

Ion milling the amorphous native metal oxides may cause them to be chemically reduced, i.e., reduce the number of oxygen atoms within the oxide. For example, $Ni_2O_3$ may be reduced to NiO. Other types of oxides such as molybdenum oxide and chromium oxide, may be similarly reduced. Metal atoms 211 are depicted similarly throughout views 201-206.

View 202 depicts the results of an in-situ ion milling operation which may use an inert gas such as argon (209, view 201) for the at least partial reduction of amorphous native metal oxides and removal of carbon-based contaminants from a surface of the stainless steel structure (including stainless steel substrate 108 and layer 210). Removal of metal oxides and carbon-based contaminants may create an exposed portion of the stainless steel structure. In certain embodiments, an exposed portion of the stainless steel structure may have a remaining metal oxide layer 210 with a thickness T2 that is less than the initial thickness T1 (view 201), corresponding to a partial removal of amorphous native metal oxides. In some embodiments, an exposed portion of the stainless steel structure may have both carbon-based contaminants and amorphous native metal oxides completely removed. Oxygen plasma (213) may be injected into the deposition chamber, and used, in conjunction with argon, in the ion milling the stainless steel structure, which may continue, with the results shown in view 203.

View 203 depicts the results of crystallizing, by oxidizing with oxygen plasma (213, view 202) injected into the deposition chamber, the exposed portion 210 (view 202) of the stainless steel structure (stainless steel substrate 108 and layer 210) to form a crystallized metal oxide bonding layer 112. Oxygen plasma (213, view 202) may react with the exposed portion of the stainless steel structure, which may include remaining amorphous native metal oxides 210 (view 202) and/or a surface of the stainless steel substrate 108, to form a crystallized metal oxide bonding layer 112.

The formation of crystalline structures in the crystallized metal oxide bonding layer 112 may be promoted by heat from an exothermic oxidation reaction between the oxygen plasma 213 (view 202) and amorphous native metal oxides 210 (view 202). Crystalline structures formed in the crystallized metal oxide bonding layer 112 may be useful as seeds (or template sites) for subsequent alumina crystallization. During the exothermic oxidation reaction, metal atoms 211 may diffuse from stainless steel substrate 108 into crystallized metal oxide bonding layer 112. Reactively sputtered alumina 215 is depicted in view 203.

View 204 depicts the results of reactive sputter deposition of alumina (aluminum oxide, $AL_2O_3$) onto the crystallized metal oxide bonding layer 112 in the presence of oxygen plasma 213 to form a graded aluminate spinel layer 114 and a first transition region 120. The graded aluminate spinel layer 114 may share crystalline structures with metal oxide bonding layer 112, and may be useful as an intermediate layer between metal oxide bonding layer 112 and a subsequent alumina layer. Graded transitions, including the first transition region 120, between the graded aluminate spinel layer 114 and adjacent layers may contribute to the overall structural integrity of the alumina-based layer structure 124.

During reactive alumina sputtering, energetic aluminum ions, in the presence of oxygen plasma, may initiate thermite-like (exothermic) reactions with metal oxides in the crystallized metal oxide bonding layer 112. These exothermic reactions may generate significant local heat, which may promote the crystallization of reactively sputtered (deposited) alumina and atomic bonding of the crystallized alumina with the crystallized metal oxide bonding layer 112. The heat from the exothermic reactions may also promote local metal (Cr, Fe, Ni, Mo) diffusion from the stainless steel substrate 108 and the crystallized metal oxide bonding layer 112 into the growing graded aluminate spinel layer 114.

As the graded aluminate spinel layer 114 grows, the number of local metal oxide molecules available to exothermically react with the sputtered alumina may decrease, and eventually local heat may no longer be released. As local heat is no longer released, a first transition region 120 is formed in a top portion of the graded aluminate spinel layer 114, and may extend from the graded aluminate spinel layer 114 into a subsequent crystalline alumina layer.

In certain embodiments, the graded aluminate spinel layer 114 may have a thickness between 5 and 20 nanometers, and may include crystallized alumina with an at least partially polycrystalline structure. The graded aluminate spinel layer 114 may also include metal diffused from the stainless steel substrate 108 surface and from the crystallized metal oxide bonding layer 112. A metal concentration gradient may exist between a bottom portion and a top portion of the graded aluminate spinel layer 114, with the metal concentration higher near the bottom portion than at the top portion. The first transition region 120 may encompass a metal concentration gradient between the graded aluminate spinel layer 114 and subsequent crystalline alumina layer.

The graded aluminate spinel layer 114 and first transition region 120 may be useful for forming a structurally integrated transition layer between the crystallized metal oxide bonding layer 112 and a subsequent crystalline alumina layer, and may contribute to the overall structural integrity of the alumina-based layer structure 124 (FIG. 1).

View 205 depicts the results of reactive sputter deposition of alumina onto the first transition region 120 in the presence of oxygen plasma 213 (view 202) to form a crystalline alumina layer 116 and a second transition region 122. The crystalline alumina layer 116 may share crystalline structures with the first transition region 120, and may be useful as an intermediate layer between the graded aluminate spinel layer 114 and a subsequent amorphous alumina layer. Graded transitions, including the second transition region 122, may contribute to the overall structural integrity of the alumina-based layer structure 124.

During reactive alumina sputtering, latent heat from prior exothermic reactions may continue to promote the crystallization of reactively sputtered (deposited) alumina and atomic bonding of the crystallized alumina with the first transition region 120. As the crystalline alumina layer 116 grows, and cools, in response to a cessation of exothermic reactions, a second transition region 122 may be formed in a top portion of the crystalline alumina layer 116, and may extend from the crystalline alumina layer 116 into a subsequent amorphous alumina layer.

The crystalline alumina layer 116 may include crystallized alumina with an at least partially polycrystalline structure. The second transition region 122 may encompass a crystalline structure gradient between the crystalline alumina layer 116 and subsequent amorphous alumina layer, with the crystalline structure proportion higher near a bottom portion than at a top portion of the second transition region 122. The crystallized alumina layer may include at least one cubic allotrope of aluminum oxide.

The crystalline alumina layer 116 and second transition region 122 may be useful for forming a structurally integrated transition layer between the graded aluminate spinel layer 114 and a subsequent amorphous alumina layer, and may contribute to the overall structural integrity of the alumina-based layer structure 124 (FIG. 1).

View 206 depicts the results of reactive sputter deposition of alumina onto the second transition region 122 through in the presence of oxygen plasma 213 (view 202) to form an amorphous alumina layer 118. The amorphous alumina layer 118 may share an amorphous structure with second transition region 122, and may be useful as a biologically and chemically inert surface layer of an alumina-based layer structure 124 (FIG. 1). The biological and chemical inertness of amorphous alumina layer 118 may make it useful as a coating for stainless steel objects and equipment used in medical applications, food, drug, pharmaceutical and chemical processing, and marine environments Amorphous alumina layer 118 may have a high hardness, resistance to wear, and be resistant to cracking, peeling, or delaminating from stainless steel substrate 108, due to the overall structural integrity of the graded layer structure 124 used to attach it to stainless steel substrate 108.

Figure 3:
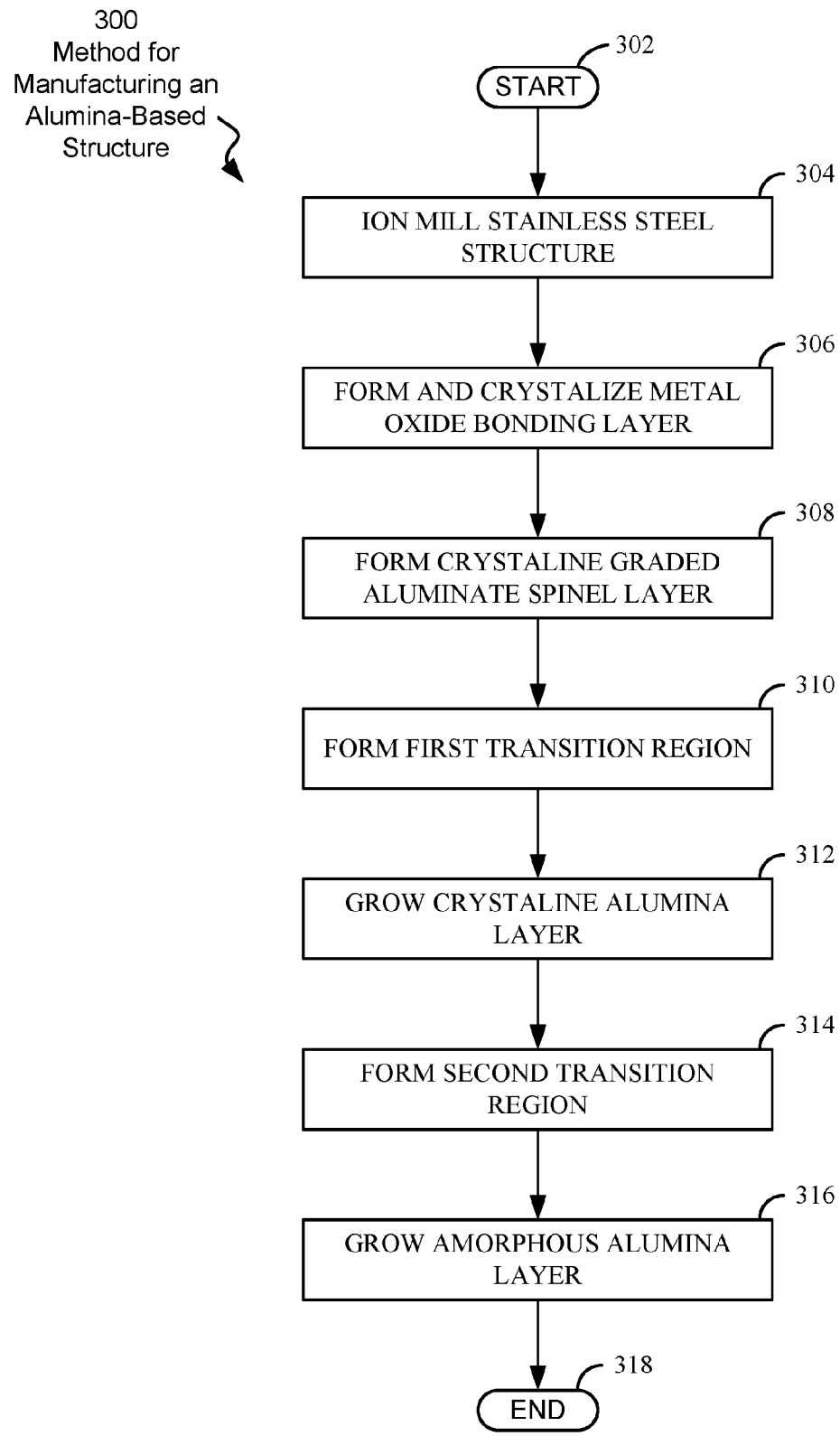
FIG. 3 is a flow diagram illustrating bonding an alumina-based layer structure to a surface of stainless steel substrate, according to embodiments.

FIG. 3 is a flow diagram consistent with FIG. 1, 2, illustrating operations for bonding an alumina-based layer structure to a surface of stainless steel substrate (108, FIG. 1), according to embodiments.

The process 300 moves from start 302 to operation 304. Operation 304 generally refers to the process operations that involve ion milling a stainless steel structure, which may correspond to the views provided by 201, 202 (FIG. 2) and their associated descriptions. The ion milling operation may be controlled through a set of parameters that define the energy, angle of incidence, and exposure time of the ion beam during the ion milling process. Ion milling may be useful in cleaning and preparing a surface of a stainless steel object for growth and deposition of subsequent material layers. Once the stainless steel structure has been ion milled, the process moves to operation 306.

Operation 306 generally refers to the process operations that involve the formation and crystallization of a metal oxide bonding layer, which may correspond to the view provided by 203 (FIG. 2) and its associated description. The metal oxide bonding layer may formed from existing amorphous native metal oxides and/or an exposed surface of the stainless steel structure, through the use of oxygen plasma in a deposition chamber. The metal oxide bonding layer may be useful in providing a crystalline layer that is structurally integrated with the stainless steel substrate surface, for further growth and formation of subsequent structural layers. Once the metal oxide bonding layer has been formed in crystallized, the process moves to operation 308.

Operation 308 generally refers to the process operations that involve forming a graded aluminate spinel layer, which may correspond to the view provided by 204 (FIG. 2) and its associated description. The graded aluminate spinel layer may be formed through the reactive sputter deposition of alumina, in conjunction with heat provided by an exothermic reaction between sputtered alumina and native metal oxides. Heat from the exothermic reaction may result in crystallization of the sputtered alumina, and may also promote diffusion of metal atoms from the stainless steel substrate surface into the graded aluminate spinel layer. After the graded aluminate spinel layer has been formed, the process moves to operation 310.

Operation 310 generally refers to the process operations that involve forming a first transition region, which may correspond to the views provided by 204 (FIG. 2) and its associated description. The first transition region denotes a metal concentration gradient between and a structurally integrated joining of the graded aluminate spinel layer and a subsequent crystalline alumina layer. After the first transition region is formed, the process moves to operation 312.

Operation 312 generally refers to the process operations that involve growing a crystalline alumina layer, which may correspond to the view provided by 205 (FIG. 2) and its associated description. The crystalline alumina layer may be formed through the reactive sputter deposition of alumina, in conjunction with latent heat provided by prior exothermic reactions between sputtered alumina and native metal oxides. The latent heat may result in crystallization of the sputtered alumina. After the crystalline alumina layer is grown, the process moves to operation 314.

Operation 314 generally refers to the process operations that involve forming a second transition region, which may correspond to the view provided by 205 (FIG. 2) and its associated description. The second transition region denotes a crystalline structure gradient between and a structurally integrated joining of the crystalline alumina layer and a subsequent amorphous alumina layer. After the second transition region is formed, the process moves to operation 316.

Operation 316 generally refers to the process operations that involve growing an amorphous alumina layer, which may correspond to the view provided by 206 (FIG. 2) and its associated description. The amorphous alumina layer may be formed through the reactive sputter deposition of alumina onto the second transition region. The amorphous alumina layer may share an amorphous structure with the second transition region, and may be useful as a biologically and chemically inert layer on a stainless steel substrate. The amorphous alumina layer may also possess properties of high hardness, and resistance to cracking, chipping and delamination from the stainless steel substrate, which may make it useful as a coating in a variety of medical, chemical and food processing applications. After the amorphous alumina layer is grown, the process 300 may end at block 318.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. An apparatus comprising:
   a stainless steel structure;
   an at least partially polycrystalline alumina-based layer structure bonded to an exposed portion of the stainless steel structure, the layer structure including:
      a crystallized metal oxide bonding layer formed on the exposed portion of the stainless steel structure;
      a graded aluminate spinel layer formed on the crystallized metal oxide bonding layer, the graded aluminate spinel layer having:
         metal diffused from the stainless steel surface;
         and an at least partially polycrystalline structure;
      a crystalline alumina layer;
      a first transition region includes a metal concentration gradient extending from the graded aluminate spinel layer to the crystalline alumina layer;
      an amorphous alumina layer; and
      a second transition region includes a crystalline structure gradient extending from the crystalline alumina layer to the amorphous alumina layer.

2. The apparatus of claim 1, wherein the apparatus is a medical device and the stainless steel structure comprises medical-grade stainless steel.

3. The apparatus of claim 1, wherein the amorphous alumina layer is biologically inert.

4. The apparatus of claim 1, wherein the alumina-based layer structure is atomically bonded to the stainless steel structure.

* * * * *